United States Patent [19]

Warnant et al.

[11] 3,932,420

[45] Jan. 13, 1976

[54] PROCESS FOR THE PREPARATION OF GLAZIOVINE

[75] Inventors: Julien Warnant, Neuilly-sur-Seine; Andre Farcilli, Rosny-sous-Bois; Italo Medici, Bondy; Edmond Toromanoff, Paris, all of France

[73] Assignee: Roussel-UCLAF, Paris, France

[22] Filed: Feb. 21, 1974

[21] Appl. No.: 444,554

[30] Foreign Application Priority Data

Feb. 28, 1973  France .............................. 73.07169

[52] U.S. Cl. ............................................. 260/289 A
[51] Int. Cl.² ........................................ C07D 217/12
[58] Field of Search ..................... 260/289 C, 289 A

[56] References Cited

OTHER PUBLICATIONS

Kametani et al. *J. Chem. Soc.* (C) pp. 2182–2184 (1967).

Ishiwata et al. *Chem. Pharm. Bull.*, 17 (6), pp. 1298–1299 (1969).

*Primary Examiner*—Donald G. Daus
*Assistant Examiner*—D. B. Springer
*Attorney, Agent, or Firm*—Bacon & Thomas

[57] ABSTRACT

Process for the preparation of glaziovine by treating N-methyl bromococlaurine in an inert organic solvent with a tin hydride tri-substituted with organic radicals in the presence of a free radical promoter.

9 Claims, No Drawings

PROCESS FOR THE PREPARATION OF GLAZIOVINE

The present invention concerns a new process for the preparation of glaziovine.

Glaziovine is an alkaloid that is extracted from the plants of the genus Ocotea and more particularly of *Ocotea Glaziovii* and possesses very interesting pharmacological properties which justifies its utilization in therapeutics. It is therefore advantageous to be able to prepare this alkaloid by a synthetic method of preparation.

But the very special tetracyclic structure of glaziovine renders the synthesis difficult. Moreover, this structure containing a spirodienone ring is not very stable in certain media and the methods of preparation actually known, both by the nature of the reactions employed and yields obtained, are of little interest on an industrial level.

There is thus described in *J. Chem. Soc.*, 1967, C, 2182, the conversion of N-methyl coclaurine to glaziovine by the action of potassium ferricyanide with a yield of the order of 1%, and in *J. Chem. Soc.*, 1971, C, 3818, the transformation of N-methyl bromococlaurine to glaziovine by irradiation in an alkaline medium with a yield of the order of 10%.

This latter method presents, moreover, the inconvenience on an industrial scale of consuming considerable irradiation energy and requiring afterwards a dissipation of this energy so as to maintain the reaction medium at a suitable temperature.

The new process for the preparation of glaziovine, which is the object of the present invention, avoids the disadvantages above. The present process, utilizing simple and easily prepared reagents, is able to be easily converted to an industrial scale and gives interesting yields. The process according to the invention comprises treating N-methyl bromococlaurine of the formula:

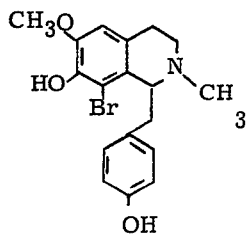

with a tin hydride tri-substituted by organic radicals, in the presence of a free radical promoter in an organic solvent or in a mixture of organic solvents, followed by isolation of the desired glaziovine having the formula:

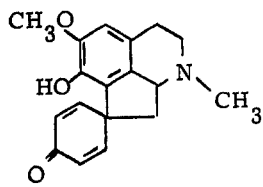

The tri-organosubstituted tin hydride is preferably the hydride of (tri-n-butyl)tin. One can equally use other hydrides of tin, such as the other trialkyl tin hydrides or the triaryl tin hydrides, as for example the triethyl tin hydride or triphenyl tin hydride.

Of the free radical initiators that can be used, lauroyl peroxide is preferred, but other organic peroxides can be used, such as benzoyl peroxide, stearoyl peroxide, or cyclohexanecarbonyl peroxide.

The organic solvent utilized is preferably benzene, but other organic solvents can be used such as, for example, toluene, tetrahydrofuran, cyclohexane, methanol, ethanol, ethyl acetate, acetone, chlorobenzene, pyridine, methylene chloride, or a mixture containing two or more of these solvents.

One can see that the above process calls for simple reactants and does not require specialized apparatus. Moreover, it permits the obtainment of glaziovine with higher yields than the known processes. It will be seen below in the example which illustrates the process that the yield is of the order of 18%. The recovery of the unreacted N-methyl bromococlaurine permits the realization of a yield of 26%.

PREPARATION OF GLAZIOVINE

A suspension of 3 grams of N-methyl bromococlaurine and 2.37 grams of (tri-n-butyl)tin hydride in 100 cc of benzene is brought to reflux. A solution of 3 grams of lauroyl peroxide in 50 cc of benzene is added over the course of an hour and the mixture refluxed for 1 hour after the end of the addition. The benzene is evaporated under vacuum and the residue that is obtained is dissolved in a mixture of ethyl acetate-methanol (7:3 v/v). The solution thus obtained is chromatographed on silica gel to give two fractions, A (3.2 g) and B (1.2 g). Thin layer chromatography shows that fraction A is rich in starting material and fraction B is rich in the expected glaziovine.

Fraction A is taken up in 10 cc of chloroform and acidified with N hydrochloric acid. The aqueous phase is neutralized with ammonia, causing crystals to precipitate, which are filtered, washed, and dried. There is thus recovered 960 mg of N-methyl bromococlaurine melting at 170°–180° C.

Fraction B is chromatographed on alumina in chloroform. The product that is obtained is crystallized by trituration with ether, giving 416 mg (17.6%) of glaziovine, being a yield of 26%, taking into account the recovered starting material. Melting point 225° C.

Analysis:

| ($C_{18}H_{19}NO_3$) | | | | | | |
|---|---|---|---|---|---|---|
| Calculated: | %C | 72.71; | %H | 6.44; | %N | 4.71 |
| Found: | | 72.6 | | 6.5 | | 4.5 |

UV spectrum (ethanol)

| Max. = 234 nm | $\epsilon = 26600$ |
|---|---|
| 290 nm (ethanol – NOAH 0.1 N) | $\epsilon = 3560$ |
| Max. = 308 nm | $\epsilon = 5400$ |

What is claimed is:

1. A process for the preparation of glaziovine comprising the steps of:
   a. treating N-methyl bromococlaurine of the formula: in an inert organic solvent with a tri-lower alkyl or triphenyl tin hydride, in the presence of a free radical promoter selected from the group consisting of lauroyl peroxide, benzoyl peroxide, stearoyl peroxide, and cyclohexanecarbonyl peroxide, and
   b. isolating the desired glaziovine.

2. The process of claim 1 wherein the hydride of tin is (tri-n-butyl)tin hydride.

3. The process of claim 1 wherein the free radical promoter is lauroyl peroxide.

4. The process of claim 1 wherein the inert organic solvent is benzene.

5. The process of claim 1, wherein the hydride of tin is triphenyl tin hydride.

6. The process of claim 1, wherein the hydride of tin is triethyl tin hydride.

7. The process of claim 1, wherein the inert organic solvent is selected from the group consisting of toluene, tetrahydrofuran, cyclohexane, methanol, ethanol, ethyl acetate, acetone, chlorobenzene, pyridine, methylene chloride, or mixtures thereof.

8. The process of claim 1, wherein the inert organic solvent is at reflux in the presence of the tin hydride and free radical promoter.

9. A process for the preparation of glaziovine comprising the steps of:
   a. treating N-methyl bromococlaurine in benzene with (tri-n-butyl)tin hydride in the presence of lauroyl peroxide and
   b. isolating the glaziovine.

* * * * *